US012694515B2

(12) United States Patent　　　　(10) Patent No.:　　US 12,694,515 B2

Heron et al.　　　　　　　　　　　(45) Date of Patent:　　　Jul. 28, 2026

(54) ERROR DETERMINATION IN BODILY FLUID TESTING

(71) Applicant: TESTCARD LTD., East Ayton (GB)

(72) Inventors: Luke Heron, East Ayton (GB);
Andrew Botham, East Ayton (GB);
Christopher Hewitt, East Ayton (GB)

(73) Assignee: TestCard Ltd., East Ayton (GB)

( * ) Notice: Subject to any disclaimer, the term of this patent is extended or adjusted under 35 U.S.C. 154(b) by 419 days.

(21) Appl. No.: 18/038,931

(22) PCT Filed: Nov. 25, 2021

(86) PCT No.: PCT/GB2021/053061

§ 371 (c)(1),
(2) Date: May 25, 2023

(87) PCT Pub. No.: WO2022/112769

PCT Pub. Date: Jun. 2, 2022

(65) Prior Publication Data

US 2024/0005485 A1　　Jan. 4, 2024

(30) Foreign Application Priority Data

Nov. 26, 2020　(GB) ...................................... 2018654

(51) Int. Cl.
G06T 7/90　　　　(2017.01)
A61B 5/00　　　　(2006.01)
G06T 7/00　　　　(2017.01)

(52) U.S. Cl.
CPC .......... G06T 7/0012 (2013.01); A61B 5/7221 (2013.01); G06T 7/90 (2017.01)

(58) Field of Classification Search
CPC ...... G06T 7/0012; G06T 7/90; H04N 1/00045

(Continued)

(56) References Cited

U.S. PATENT DOCUMENTS

| 2015/0359458 | A1 | 12/2015 | Erickson et al. | |
| 2020/0211228 | A1 | 7/2020 | Adiri et al. | |
| 2022/0072532 | A1 * | 3/2022 | Mccord ................. | G01J 3/0286 |

FOREIGN PATENT DOCUMENTS

| EP | 2916117 A1 * | 9/2015 | ............. G01N 33/52 |
| TW | I695169 B * | 6/2020 | |

OTHER PUBLICATIONS

Karlsen Haakon et al: "Smartphone-Based Rapid Screening of Urinary Biomarkers", IEEE Transactions on Biomedical Circuits and Systems, IEEE, US, vol. 11, No. 2, Apr. 1, 2017, 9 pages.

(Continued)

*Primary Examiner* — Jamares Q Washington

(74) *Attorney, Agent, or Firm* — Brooks, Cameron & Huebsch, PLLC

(57)　　　　　ABSTRACT

There is provided a method for determining an error in image data of bodily fluid testing equipment. The method comprises detecting (S304) a first colour of a first testing region in the image data, comparing (S306) the detected first colour to reference colours, determining (S308) respective difference scores between the detected first colour and the reference colours, determining (S310) a closest reference colour wherein the closest reference colour has a lowest difference score, determining (S312) whether the difference score between the detected first colour and the closest reference colour is less than a predetermined maximum difference score, performing (S380) a first action when the difference score is less than the predetermined maximum difference score, and determining (S390) that there is an error in the first testing region in the image data and performing a second action when the difference score is not less than the predetermined maximum difference score.

13 Claims, 7 Drawing Sheets

(58) Field of Classification Search
USPC ................................................. 382/128, 165
See application file for complete search history.

(56) References Cited

OTHER PUBLICATIONS

International Search Report and Written Opinion from related PCT Application No. PCT/GB2021 /053061, dated Mar. 1, 2022, 18 pages.

\* cited by examiner

ERROR DETERMINATION IN BODILY FLUID TESTING

FIELD OF INVENTION

The present disclosure relates to bodily fluid testing equipment and more specifically error determination in image data of bodily fluid testing equipment in a bodily fluid testing process.

BACKGROUND

Bodily fluids, such as urine, are typically tested at a medical establishment such as a hospital. Such testing requires a patient to visit a doctors' surgery or hospital to deposit a sample of bodily fluid, and then wait for results. In many cases, waiting for the results can take several days. There is a need to provide a more user-friendly and efficient process for bodily fluid testing.

The reliability of bodily fluid testing is important, particularly with regard to the determination of errors during the processing of a bodily fluid test that might affect the reliability of the result. There is a need to address the determination of errors in bodily fluid testing processes.

An object of the present invention is, therefore, to address such challenges amongst others.

SUMMARY

In a first aspect, there is provided a method for determining an error in image data of bodily fluid testing equipment in a bodily fluid testing process, the image data captured by an electronic device, and the method comprising: detecting a first colour of a first testing region in the image data, comparing the detected first colour to one or more reference colours, determining respective difference scores between the detected first colour and each of the one or more reference colours, determining a closest reference colour of the one or more reference colours, wherein the closest reference colour has a lowest difference score, determining whether the difference score between the detected first colour and the closest reference colour is less than a predetermined maximum difference score, performing a first action when the difference score between the detected first colour and the closest reference colour is less than the predetermined maximum difference score, and determining that there is an error in the first testing region in the image data and performing a second action when the difference score between the detected first colour and the closest reference colour is not less than the predetermined maximum difference score.

In this way, errors from external sources can be determined in a bodily fluid testing process. Determining such errors allows for them to be accounted for, thereby improving the reliability of the output of the bodily fluid testing process.

Preferably, the first testing region is a first colour change pad configured to change colour in presence of one or more specific indicators.

In this way, errors can be determined in bodily fluid testing processes for a number of conditions. Such conditions can include, but are not limited to, urinary tract infections, diabetes, or glucose levels for diabetic screening or monitoring, and metabolic disorders, kidney disease, liver disease, dietary disorders, and pregnancy term complications, amongst others.

Preferably, the method further comprises: determining whether the closest reference colour belongs to a set of one or more predetermined reference colours associated with the first testing region, and determining that there is an error in the first testing region in the image data and performing the second action when the closest reference colour does not belong to the set of one or more predetermined reference colours.

In this way, the method can determine errors when a closely matching reference colour is identified, but it is not a reference colour that is relevant for the first testing region. For example, the user may have their thumb over the first testing region, and the colour of their thumb may closely match one of the reference colours, but this is not a colour which is relevant for determining whether an indicator has interacted with the first testing region. This can improve the reliability of the output of the bodily fluid testing process.

Preferably, the first action comprises determining whether an indicator has interacted with the first testing region based upon the detected first colour.

In this way, the determination of whether an indicator has interacted with the first testing region occurs when an error has not been determined. This can improve the reliability of the output of the bodily fluid testing process as erroneous data is accounted for.

Preferably, the bodily fluid testing equipment comprises a plurality of further testing regions having respective further colours in the image data, and the first action comprises repeating the steps of the method for determining an error in image data of bodily fluid testing equipment in a bodily fluid testing process for each respective further testing region, and determining whether an indicator has interacted with the first testing region based upon the detected first colour and whether respective indicators have interacted with the further testing regions based upon the detected respective further colours when the difference scores between each respective detected further colour and the respective closest reference colour is less than a predetermined maximum difference score.

In this way, when there is a plurality of testing regions, the determination of whether respective indicators have interacted with the respective testing region occurs when an errors have not been determined in any the image data of any of the testing regions. This can improve the reliability of the output of the bodily fluid testing process as erroneous data is accounted for.

Preferably, repeating the steps of the method for determining an error in image data of bodily fluid testing equipment in a bodily fluid testing process for each respective further testing region, comprises for a second bodily fluid testing region: detecting a second colour of a second testing region in the image data, comparing the detected second colour to one or more reference colours, determining respective difference scores between the detected second colour and each of the one or more reference colours, determining a closest reference colour of the one or more reference colours, wherein the closest reference colour has a lowest difference score, determining whether the difference score between the detected second colour and the closest reference colour is less than a predetermined maximum difference score, performing a first action when the difference score between the detected second colour and the closest reference colour is less than the predetermined maximum difference score, and determining that there is an error in the second testing region in the image data and performing a second action when the difference score between the detected second colour and the closest reference colour is not less than the predetermined maximum difference score.

Preferably, repeating the steps of the method for determining an error in image data of bodily fluid testing equipment in a bodily fluid testing process for each respective further testing region, comprises for a third bodily fluid testing region: detecting a third colour of a third testing region in the image data, comparing the detected third colour to one or more reference colours, determining respective difference scores between the detected third colour and each of the one or more reference colours, determining a closest reference colour of the one or more reference colours, wherein the closest reference colour has a lowest difference score, determining whether the difference score between the detected third colour and the closest reference colour is less than a predetermined maximum difference score, performing a first action when the difference score between the detected third colour and the closest reference colour is less than the predetermined maximum difference score, and determining that there is an error in the third testing region in the image data and performing a second action when the difference score between the detected third colour and the closest reference colour is not less than the predetermined maximum difference score.

Preferably, repeating the steps of the method for determining an error in image data of bodily fluid testing equipment in a bodily fluid testing process for each respective further testing region, comprises for a nth bodily fluid testing region: detecting an nth colour of an nth testing region in the image data, comparing the detected nth colour to one or more reference colours, determining respective difference scores between the detected nth colour and each of the one or more reference colours, determining a closest reference colour of the one or more reference colours, wherein the closest reference colour has a lowest difference score, determining whether the difference score between the detected nth colour and the closest reference colour is less than a predetermined maximum difference score, performing a first action when the difference score between the detected nth colour and the closest reference colour is less than the predetermined maximum difference score, and determining that there is an error in the nth testing region in the image data and performing a second action when the difference score between the detected nth colour and the closest reference colour is not less than the predetermined maximum difference score.

Preferably, the second action comprises: configuring the electronic device to indicate that the bodily fluid testing process cannot be carried out.

In this way, the user of the electronic device can be made aware that an error has been determined.

Preferably, wherein the second action comprises: configuring the electronic device to capture replacement image data.

In this way, another attempt can be made at the bodily fluid testing process, using replacement image data. This can reduce the need to use new equipment for a repeated bodily fluid test following an error, and can reduce the need to produce another bodily fluid sample for the testing process. This can also reduce the time taken to achieve a useful result from the test, following an error. The efficiency of the bodily fluid testing process is therefore improved.

Preferably, the electronic device is configured to capture the replacement image data only within a predetermined time limit.

Some testing regions may degrade in the presence of moisture, or following exposure to environmental conditions. Limiting the time in which a replacement image can be captured minimises any degradation of the testing region and therefore improves the reliability of the image data when recaptured.

Preferably, the method further comprises: detecting an updated first colour of the first testing region in the replacement image data, comparing the detected updated first colour to the one or more reference colours, determining respective difference scores between the detected updated first colour and each of the one or more reference colours, determining an updated closest reference colour of the one or more reference colours, wherein the updated closest reference colour has a lowest difference score, determining whether the difference score between the detected updated first colour and the updated closest reference colour is less than the predetermined maximum difference score, performing a third action when the difference score between the detected updated first colour and the updated closest reference colour is less than the predetermined maximum difference score, and determining that there is an error in the first testing region in the replacement image data and performing a fourth action when the difference score between the detected updated first colour and the updated closest reference colour is not less than the predetermined maximum difference score.

In this way errors from external sources can be determined in replacement image data in a bodily fluid testing process, following the earlier determination of an error in image data. Determining such errors allows for them to be accounted for, thereby improving the reliability of the output of the bodily fluid testing process.

Preferably, the third action comprises determining whether an indicator has interacted with the first testing region based upon the detected updated first colour, and/or the fourth action comprises configuring the electronic device to indicate that the bodily fluid testing process cannot be carried out.

In this way, the determination of whether an indicator has interacted with the first testing region occurs when an error has not been determined. This can improve the reliability of the output of the bodily fluid testing process as erroneous data is accounted for. When an error is determined, the user of the electronic device can be made aware of the error.

Preferably, the respective difference scores between the detected first colour and each of the one or more reference colours are determined as Delta E values between the detected first colour and each of the one or more reference colours.

In this way precise differences between colours can be determined. This improves the reliability of the bodily fluid testing processing.

Preferably, the method is performed at the electronic device, or the image data is transmitted from the electronic device to a server and the method is performed at the server.

In this way, the processing can be carried out locally at the electronic device. This is beneficial when a network connection may not be available. Alternatively, carrying out the processing at a server can reduce the processing burden on the electronic device. Additionally, carrying out the processing at a server can allow for a consistent colour spectrum to be used to ensure that consistent results are achieved. Preferably the server may utilise a Python application programming interface.

In a second aspect, there is provided an electronic device configured to perform the method of the first aspect.

In a third aspect, there is provided a server configured to perform the method of the first aspect.

In a fourth aspect, there is provided a non-transitory computer-readable medium storing instructions which when executed by one or more processors cause the processors to perform the method of the first aspect.

BRIEF DESCRIPTION OF THE DRAWINGS

Embodiments of the invention are now described, by way of example, with reference to the drawings, in which.

DETAILED DESCRIPTION

Figure 1A:
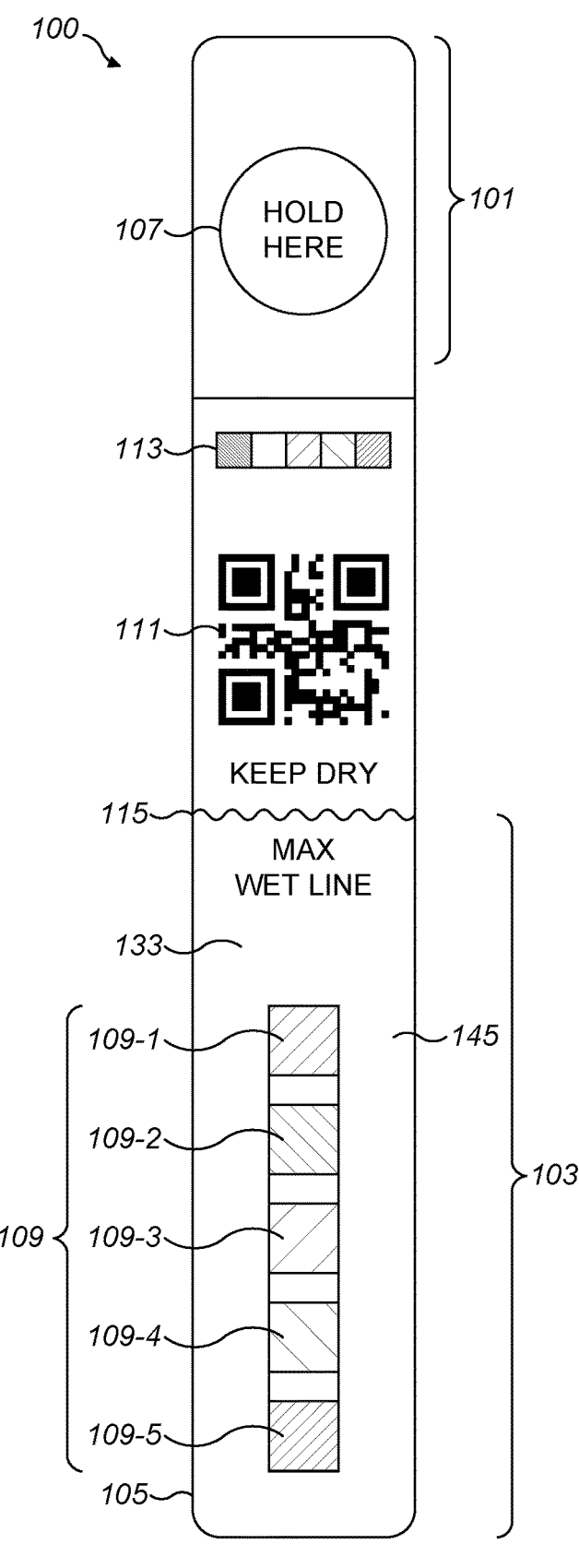
FIG. 1A is a plan view of an application-analysable bodily fluid testing equipment.
Figure 1B:
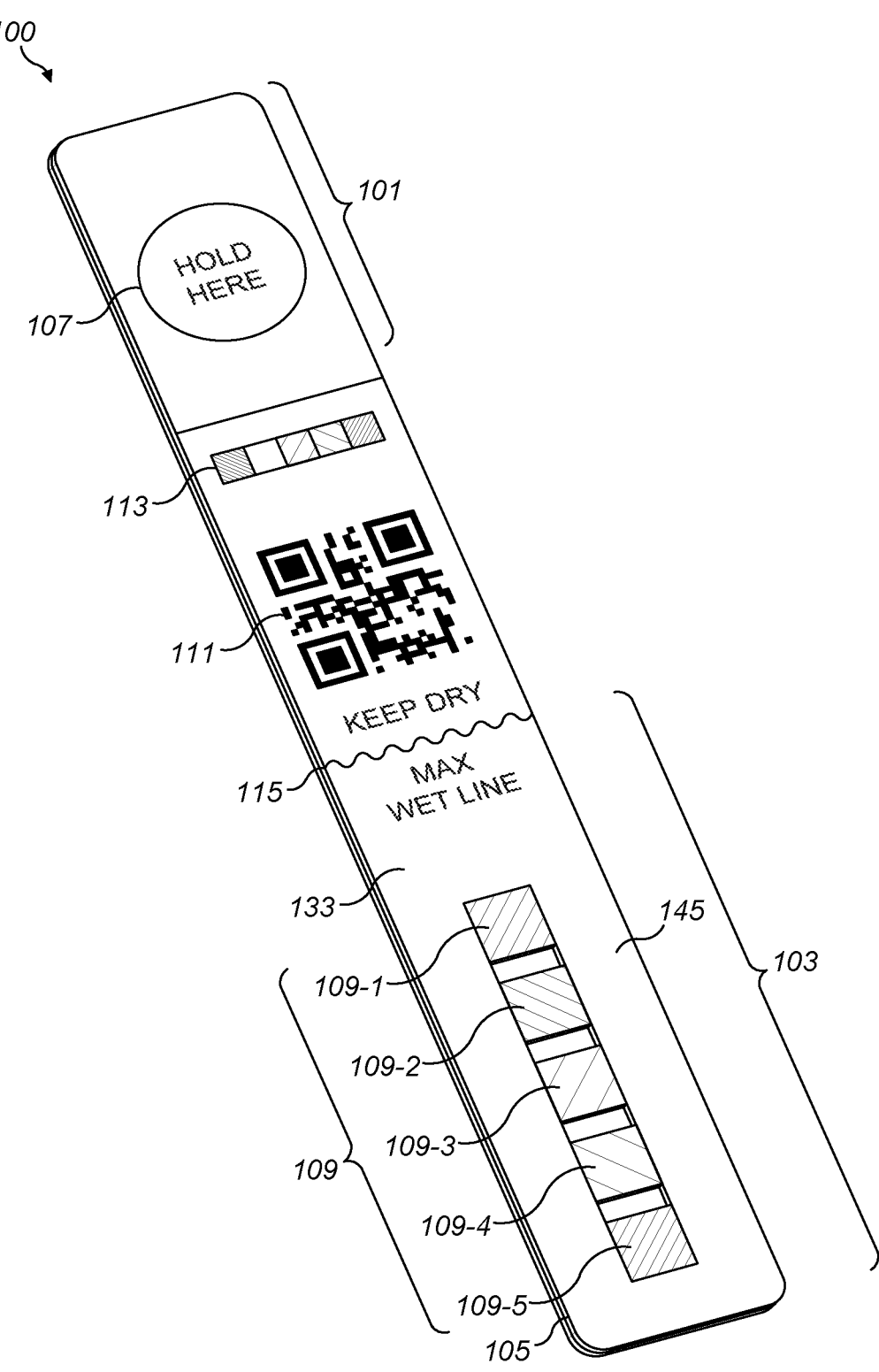
FIG. 1B is a perspective view of an application-analysable bodily fluid testing equipment.
Figure 1C:
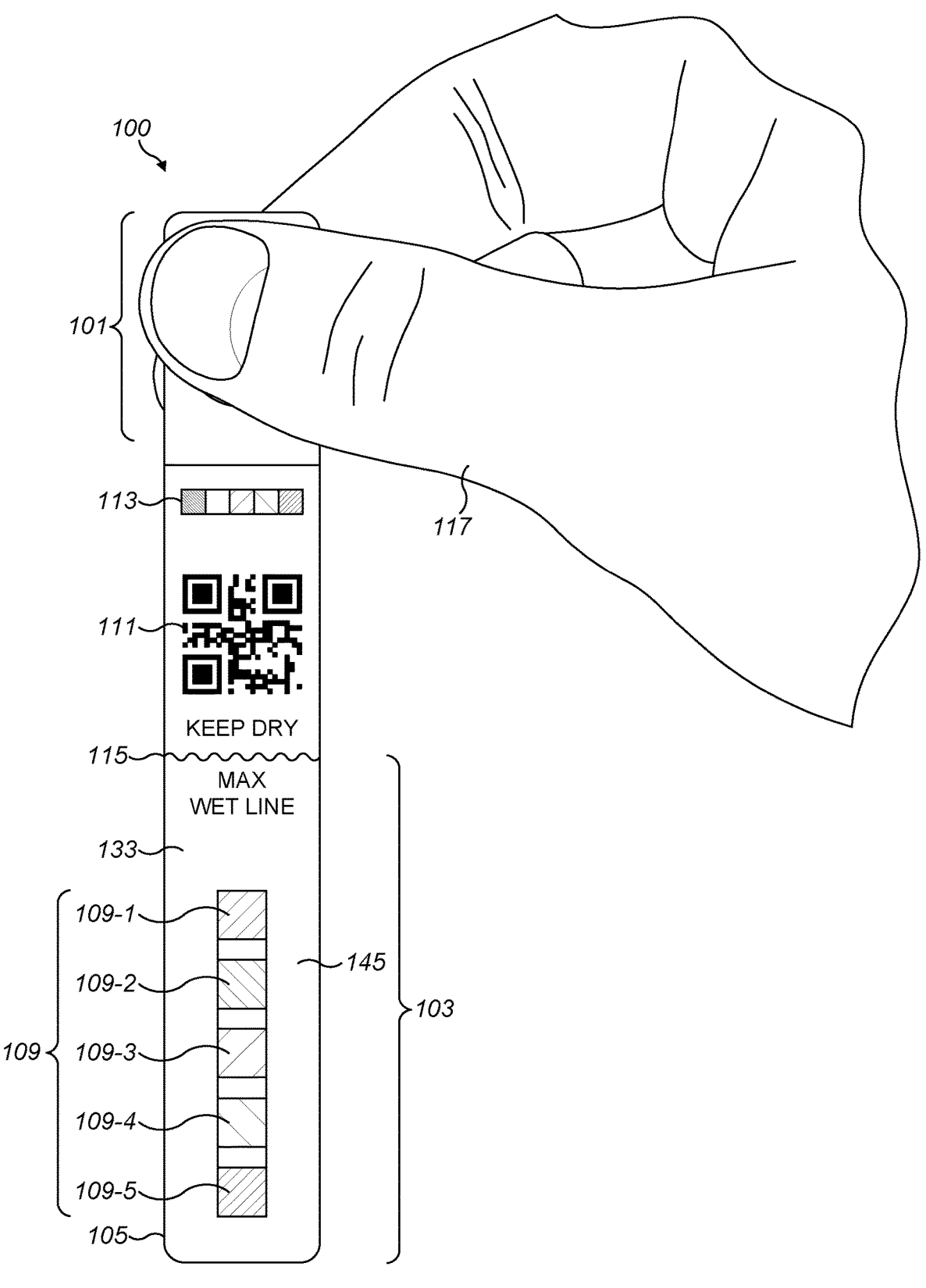
FIG. 1C is a diagram of a hand holding an application-analysable bodily fluid testing equipment.

FIGS. 1A to 1C show an application-analysable bodily fluid testing equipment 100 according to embodiments of the present disclosure. In the present description, the equipment is referred to as a card 100. It will be readily understood, however, that the equipment can be any other shape, size or material suitable to carry out its purpose.

The bodily fluid testing card 100 is arranged such that a user can hold a holding area 101 of the card 100 whilst applying a bodily fluid, such as urine, to a testing area 103 of the card 100. In the present description, the bodily fluid is described as urine. However, the skilled person will readily understand that the embodiments described can also be used with other bodily fluids, such as blood or saliva, or any other suitable bodily fluid. The testing area 103 has one or more colour change pads 109, defining one or more testing regions, which interact with identifiers of conditions in the urine. Image data of the card 100 is captured whilst the user is still holding the holding area 101 using a camera of an electronic device such as a smartphone. An application executable on the smartphone implements one or more algorithms to analyse the captured image data and output a result. The result indicates whether or not a condition is present in the user's bodily system based upon indicators of the condition in the user's urine which have interacted with the pads 109 in the testing area 103.

The bodily fluid testing card 100 has a body 105 with an elongate shape which acts as a support structure for the colour change pad(s) 109. The body 105 is planar in shape, in that the length and width of the card 100 is considerably greater than the thickness. This is advantageous as the equipment can be efficiently packaged and occupy minimal space. The body 105 can be made from any suitable material for the application of fluid; examples of which can include paper, card, plasticised card, polymer(s) or composites/combinations thereof. The body 105 can be formed of a single layer of the aforementioned materials, alternatively the body 105 can be made of two or more layers of the aforementioned materials adhered together to form a multi-layer structure.

A first end portion of the card 100 is defined as a holding area 101. A second end portion, opposite the first end portion, is defined as a testing area 103.

The holding area 101 includes a handling indicator 107 defining a sub-region of the holding area 101 at which a user of the card 100 should apply a finger/thumb 117 when using the card 100. FIG. 1C shows card 100 being held by the handling indicator 107. The handling indicator 107 comprises indicia such as textual information indicating to the user to hold the card 100 at the handling indicator 107 when in use. The textual information can be surrounded by an enclosed shape, such as a circle, to clearly convey the specific area the user should apply their thumb 117. The handling indicator 107 is printed on a surface 133 of the body 105. Alternatively, the handling indicator 107 can be embossed, debossed, or presented in any other suitable manner on the surface 133. Advantageously, the indicia guide the user as to where the equipment should be held for optimal use.

The surface 133 includes machine readable information 111, such as a QR code. The application scans the QR code 111 to determine the specific test to be performed, as well as reagent lot characteristics and expiry information, which analysis is to be carried out, and to determine specific parameters for scanning or analysing the testing equipment 100. Such parameters can include, but are not limited to, the size and/or aspect ratio of the card, the layout of colour change pads 109, sizes of the colour change pads 109, distances between the colour change pads 109, distances between the colour change pads 109 and other features on the card such as the QR code 111, the type or types of colour change pad 109, reference colours for the colour change pads 109, and others. The application uses information from the QR code 111 to access equipment information associated with the QR code 111 from storage that is associated with and accessible by the application. The equipment information can include specific parameters relating to the card 100. The parameters can also include specifics relating to the error determination process described with reference to FIGS. 2 to 4. The location of the QR code 111 can be used by the application in determining the location of the pads 109.

The surface 133 can also include a colour reference chart 113. The colour reference chart 113 is a series of cells that can be printed on in the holding area 101 in colours which can act as colour reference colours for quality control of picture and/or camera performance. In the example of FIGS. 1A-C, the colour reference chart 113 comprises a single strip of cells arranged in a line above the QR code 111; the cells colours may include (but not limited to) primary colours and/or key colours to support colour transition points on the pads.

The testing area 103 includes testing pads 109 that are sensitive to analytes measurable in urine. The testing area 103 is arranged on the same surface 133 of the body 105 as the handling indicator 107. The testing area 103 is described in more detail subsequently.

A maximum depth line 115 is presented on the same surface 133 of the body 105 as the handling indicator 107. The maximum depth line 115 indicates the maximum depth to which the card 100 should be dipped in a urine sample or below which the strip can be exposed for direct application of urine.

The testing area 103 optionally can further include a test pad which has a low tolerance for exposure to ambient moisture (pre-dipping). Which pad is used depends on the configuration of the test but may include leucocytes, nitrites, or protein. The application can utilise an algorithm with these pads to detect for the presence of moisture which can be indicative of the integrity of the card. This may indicate damage or tampering to the packaging, that the strip has been left outside of the packaging for an extended period prior to use, or that the strip has been previously dipped or wetted.

The testing area 103 comprises testing region(s) in the form of colour changing pads 109 which change colour in response to the presence of indicators in applied urine. The testing pads can be surrounded or bordered by a background area 145. Urine can be applied directly to colour change pads 109 by expulsion from a user, or the colour change pads 109 can be dipped into a urine sample by dipping the card 100 into the urine sample. Colour change pads 109 can be used in testing for conditions including urinary tract infections, diabetes, or glucose levels for diabetic screening or monitoring, and metabolic disorders, kidney disease, liver disease, dietary disorders, and pregnancy term complications, amongst others. In an example, the colour change pads can detect, amongst others, the presence of leucocytes, nitrites, protein, glucose, ketones, urobilinogen, bilirubin, erythrocytes, haemoglobin, creatinine, microalbumin, as well measure specific gravity and pH. These can be used in combination, for example, to identify a pathological condition relevant to a disease. Reagents within the colour change pads react with an analyte (or indicator) related to the condition being tested for (if present in the urine or bodily fluid) to create a colour change. The type and extent of the colour can be indicative of the amount of analyte present. In an example, a testing equipment for a urinary tract infection uses a leucocyte pad, a nitrite pad and a pH pad. The number of colour change pads 109 required can vary with the test for which the colour change pads are to be used.

In operation, a user holds the card 100 by the handling indicator 107 and applies urine (or any other suitable bodily fluid) by direct expulsion from their body, or by dipping the card 100 into urine. In response to indicators in the urine, the colour change pad(s) 109 may change colour.

Whilst still holding the card 100 the user opens a related application on an electronic device, such as a smartphone. The application prompts the user to capture an image of the card 100, using a camera on the electronic device. The application can display a frame or outline on the device display to guide the user to correctly orientate the card 100 for the image capture. The application may display a countdown timer to the user prior to capturing the image. The time period of the countdown timer can correspond to an amount of time needed for a colour to sufficiently change (i.e. the time it takes for the result to develop) in colour change pads 109. The length of time can be set according to the type of test being carried out, as determined from the machine readable information 111. In some cases, after an extended period of time, the applied bodily fluid can cause the testing regions to degrade, as such the application additionally can limit the period of time after applying the bodily fluid in which the image may be captured so as to maintain the reliability of the test.

Figure 2:
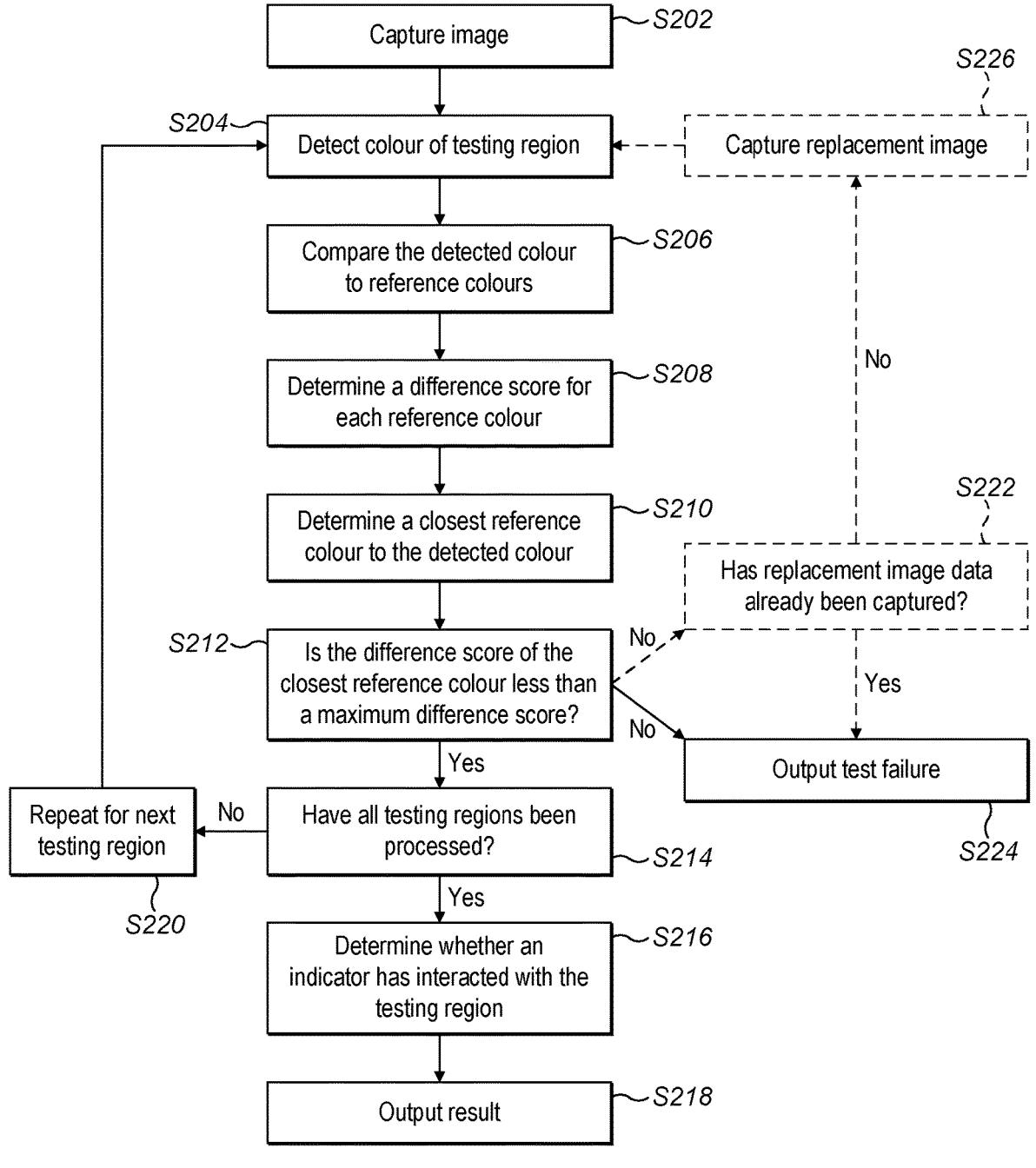
FIG. 2 is a flow diagram of processing steps involved in a bodily fluid testing process.

FIG. 2 shows an overall process flow for a bodily fluid testing process, using image data, that includes the determination of whether one or more errors are present in the image data.

At step S202 the application prompts the user to capture an image (also referred to as image data) of the card 100, as described above, using a camera integrated into the electronic device upon which the application is loaded.

The application then determines the location of the testing regions 109 (or colour change pads) of the card 100 in the image data. In the example of FIGS. 1A to 1C, the card has five testing regions 109: a first testing region 109-1, a second testing region 109-2, a third testing region 109-3, a fourth testing region 109-4, and a fifth testing region 109-5. The card 100 could, however, comprise any suitable number of testing regions. The application can also determine the location of the colour reference chart 113 and the background area 145. In an example, the colour reference chart 113 can include one or more calibration colours printed on the card 100, and the background area 145 can be white in colour. Based upon the determined locations of the colour reference chart 113 and the background area 145 (preferably a dry region above the maximum depth line 115), the application can extract calibration colours that are 'on device' (that is, reference colours included on the card) from the image data. These can then be used to correct for ambient lighting conditions, as described with reference to S203.

Optionally, at step S203, a white balance correction is executed. S203 is not shown in FIG. 2, but it will be readily understood that it can be included between steps S202 and S204. The white balance correction process can be executed by the application to account for ambient lighting (i.e. external lighting) incident on the card 100, when the image data is captured, affecting the colours in the image data. The white balance correction process is used to calculate a white balance correction parameter that accounts for the difference between the extracted colour of the white background area 145 and/or the extracted colour(s) of the one or more calibration colours in the colour reference chart 113, and expected colours of these regions under natural lighting. In this way, the white balance correction parameter can be used to correct the image data to account for warm or cold external lighting incident on the card when the image data was captured. This can improve the results of the overall bodily fluid testing process. The detected colours of the testing regions (described with reference to S204) can be corrected using the white balance correction parameter to correct colours affected by warm or cold ambient lighting to their natural colour before the error determination (described with reference to S206-S214) is carried out.

At step S204, the application detects a first colour of the first testing region 109-1 in the image data. It will be understood that the first testing region can be any of the testing regions, and is not limited to a specific testing region such as the uppermost testing region as in FIGS. 1A to 1C. Likewise, the second testing region, third testing region, and so on, can be any of the testing regions.

At step S206, the application compares the first colour to one or more reference colours. In a particular example, these colours are a series of reference colours stored in memory accessible by the application.

At step S208, the application determines respective difference scores between the detected first colour and each of the one or more reference colours.

In some examples, steps S206 and S208 can be considered as one single step with the processes of steps S206 and S208 occurring at the same time.

In an example, the difference score between the detected first colour and each of the one or more reference colours can be determined using a colour distance metric. In colour space, the distance between two colours can be determined;

this distance represents the difference between the two colours. For example, each colour can be at a point in colour space, and the distance between two points, based upon their coordinates in the colour space, relates to the difference between two colours. An exemplary distance metric using such an approach is the Delta E metric, also known as CIELAB ΔE*.

The difference scores between the detected first colour and each of the one or more reference colours can be determined based upon the distances between the colours using a Delta E metric, such as the CIE 2000 Delta E formula (also known as CIEDE2000).

Table 1 presents exemplary Delta E values, and how such differences can be perceived.

TABLE 1

| Delta E Value | Perception |
| --- | --- |
| ≤1 | Not perceptible by human eyes |
| 1 to 2 | Perceptible through close observation |
| 2 to 10 | Perceptible at a glance |
| 11 to 49 | Colours are more similar than opposite |
| 100 | Colours are exact opposite |

The application uses the Delta E metric, such as the CIE 2000 Delta E formula, to calculate a Delta E value between the detected first colour and each of the reference colours, thereby providing the respective difference scores between the detected first colour and the one or more reference colours. That is, the respective difference scores between the detected first colour and each of the one or more reference colours are determined as a Delta E value between the detected first colour and each of the one or more reference colours.

At step S210, the application determines a closest reference colour of the one or more reference colours to the detected first colour. The closest reference colour to the detected first colour has the lowest difference score of the determined difference scores. In an example, the reference colour for which the lowest Delta E value is determined when compared to the detected first colour is the closest reference colour to the detected first colour. Conceptually, in colour space, the closest reference colour to the detected first colour is the reference that is at the smallest distance from the detected first colour.

At step S212, the error determination is carried out. At step 212, the application determines whether the difference score between the detected first colour and the closest reference colour is less than a predetermined maximum difference score. In some examples, the determined Delta E value may be between 0 and 10 for an effective bodily fluid testing process; in particular, the predetermined maximum Delta E value may be between 5 and 10. The predetermined maximum difference score represents a threshold difference between the detected first colour and the closest reference colour. When the difference score between the detected first colour and the closest reference colour is less than the maximum difference score the closest reference colour is an allowable closest reference colour, and an error is not determined. When the difference score between the detected first colour and the closest reference colour is not less than the maximum difference score the closest reference colour is an unallowable closest reference colour, and an error is determined.

For completeness, in some examples, a difference score being less than a maximum difference score encompasses the difference score being less than or equal to the maximum difference score, and a difference score being not less than a maximum difference score encompasses the difference score being greater than the maximum difference score. Alternatively, in other examples, a difference score being not less than a maximum difference score encompasses the difference score being greater than or equal to the maximum difference score.

The maximum difference score can be based upon a maximum Delta E value that is allowable between detected first colour and the closest reference colour. When the Delta E value between the detected first colour and the closest reference colour is less than the maximum allowable Delta E value, the closest reference colour is an allowable closest reference colour and an error is not determined. When the Delta E value between the detected first colour and the closest reference colour is not less than the maximum allowable Delta E value, the closest reference colour is an unallowable closest reference colour and an error is determined.

Conceptually, in colour space, a boundary can be projected around the detected first colour. This boundary represents the furthest distance the closest reference colour can be from the detected first colour whilst still being allowably different to the detected first colour. In other words, the boundary represents the maximum allowable difference, or the maximum Delta E value, between the detected first colour and the closest reference colour. When the closest reference colour falls within the projected boundary, the closest reference colour is an allowable closest reference colour and an error is not determined. When the closest reference colour does not fall within the projected boundary, the closest reference colour is an unallowable closest reference colour and an error is determined. In an alternative conceptual construction, the boundary can be projected around the closest reference colour, with the detected first colour being allowably different to the closest reference colour when it falls within the boundary.

The predetermined maximum difference score (for example a predetermined maximum Delta E value) can be stored in memory accessible to the application. In an example, the maximum difference score for the first testing region 109-1 (and respective maximum difference scores for the further testing regions 109-2, 109-3, 109-4, 109-5) can be determined using information associated with the QR code 111. The maximum difference score may vary between types of colour change pad, due to differences in allowable tolerances; alternatively, all of the colour change pads may have the same maximum difference score. When the difference score between the detected first colour and the closest reference colour is less than the predetermined maximum difference score, the detected first colour can be considered as suitable for use in the determination of whether the indicator for which the first testing region 109-1 is configured has interacted with the first testing region 109-1. That is, an error has not been determined. In this case, the process continues to step S214. When the difference score between the detected first colour and the closest reference colour is not less than a predetermined maximum difference score, the detected first colour can be considered as unsuitable for use in the determination of whether the indicator for which the first testing region 109-1 is configured has interacted with the first testing region 109-1. That is, an error has been determined. In this case, the process continues to step S224 or optionally step S222 (described subsequently).

In an example, the urine applied to the card may have a strong colour, or could include blood, which could alter the colour of the testing region thereby making the testing process ineffective. In another example, lighting or shadowing incident on the card might affect the colouring in the image. In a further example, a user may be obscuring the testing region with their finger or thumb, thereby causing the wrong colour to be detected. The error determination addresses these issues.

The predetermined maximum difference score (for example the predetermined maximum Delta E value) can be determined in a training phase, for example before the end user operates the application. Using multiple images of testing strips, expected variations of detected colours of the testing regions in the image data, within allowable tolerances, can be determined. The allowable tolerance corresponds to the maximum difference score. In an example, an allowable tolerance might be 15% for each different calibration concentration. The maximum difference score can be different for different types of testing region (for example, different types of colour change pad); that is, some types of colour charge pad may have a higher or lower allowable tolerance than others.

Optionally, at step S212, the application can also determine whether the closest reference colour belongs to a set of one or more predetermined reference colours associated with the first testing region 109-1. That is, the application stores a set of predetermined reference colours that could feasibly be associated with each testing region. In an example, the set of predetermined reference colours for the first testing region 109-1 (and respective sets of predetermined reference colours for the further testing regions 109-2, 109-3, 109-4, 109-5) can be stored in memory accessible to the application and can be determined using information associated with the QR code 111. When the detected first colour does belong to the set of predetermined reference colours associated with the first region, the process progresses to step S214. That is, an error has not been determined. When the detected first colour does not belong to the set of predetermined colours, it may be that the detected first colour is closely matching to an unexpected reference colour. That is, an error has been determined. In this case, to avoid an erroneous analysis of the first testing region 109-1, the process progresses to step S224 or optionally step S222 (described subsequently). In this way, a two-factor error determining process is achieved. Firstly, the closest reference colour to the detected first colour is determined, and if the difference between the closest reference colour and the detected first colour is not less than a maximum difference, an error is determined. Secondly, if the difference between closest reference colour to the detected first colour is below the maximum, but the closest reference colour is not a reference colour that is expected for the first testing region 109-1, an error is determined. This can be used to determine errors when a closely matching reference colour is identified, but it is not a reference colour that is relevant for the first testing region 109-1. For example, the user may have their thumb over the first testing region 109-1, and the colour of their thumb may closely match one of the reference colours, but this is not a colour which is relevant for determining whether an indicator has interacted with the first testing region 109-1.

At step S214 the application determines whether all of the testing regions in the image of the card have been processed. That is, the application determines whether there are any further testing regions for which the colour should be detected, compared to the reference colours to determine difference scores, for which the closest reference colour should be determined, and for which it should be determined if the difference score is less than a respective predetermined maximum difference score associated with the testing region. In an example, the application can determine how many testing regions are to be processed using information associated with the QR code 111. In other example, the application can determine how many testing regions are to be processed based a number that are determined in the image when the application carries out the testing region locating step. When there are further testing regions to be processed, the process continues to step S220 and these further testing regions are processed. When there are no further testing regions to be processed, i.e. when all of the testing regions have been processed or when there is only one testing region, the process continues to step S216, and determines whether respective indicators have interacted with the respective testing regions. In the example of FIGS. 1A to 1C, there are five testing regions. After processing the first testing region 109-1, the application repeats steps S204 to S214 for each of the further testing regions, starting with the second testing region 109-2, and then progressing through the third testing region 109-3, the fourth testing region 109-4 and the fifth testing region 109-5 before determining that all of the testing regions have been processed. It will be understood that the testing regions can be processed in any order. It will also be understood that there can be any suitable number of testing regions, including only one testing region (in which case the process automatically continues to S216).

At step S220 the processing steps of S204 to S212, as described above with reference to the first testing region 109-1, are repeated for the second testing region 109-2 in the image and are summarised below. It will be understood that the processing steps described with reference to S204 to S212 for the first testing region 109-1 are applied to the second testing region 109-2 (and then the other further testing regions as appropriate).

When step S204 is repeated for the second testing region 109-2, the application detects a second colour of the second testing region 109-2 in the image data.

When step S206 is repeated for the second testing region 109-2, the application compares the detected second colour to the one or more reference colours.

When step S208 is repeated for the second testing region 109-2, the application determines respective difference scores between the detected second colour and each of the one or more reference colours.

When step S210 is repeated for the second testing region 109-2, the application determines a closest reference colour of the one or more reference colours to the detected second colour. The closest reference colour to the detected second colour has a lowest difference score compared to the detected second colour.

When step S212 is repeated for the second testing region 109-2, the application determines whether the difference between the detected second colour and the closest reference colour to the detected second colour is less than a predetermined maximum difference score. The predetermined maximum difference score for the further testing regions 109-2, 109-3, 109-4, 109-5 can be the same maximum difference score as used for the first testing region 109-1; alternatively, different respective maximum difference scores can be associated specifically with each testing region. When the difference score is less than the maximum difference score, for the second testing region 109-2, the process continues to step S214. When the difference score is not less than the maximum difference score, for the second testing region 109-2, the process continues to step S224 or optionally S222.

Upon reaching step S214, after processing the second testing region 109-2, in the example of FIGS. 1A to 1C, the process continues to step S220 and repeats steps S204 to S212 for the third testing region 109-3, the fourth testing region 109-4 and the fifth testing region 109-5. More generally, the steps S204 to S212 can be repeated for any number of testing regions 109 that are present in the image of the card 100. That is, when a bodily fluid testing card as n testing regions, steps S204 to S212 are repeated for the second testing region 109-2 to the nth testing region at step S220.

When it is determined, at S214, that all of the testing regions in the image data have been processed, the process flow continues to step S216.

At step S216 the application determines whether indicator (s) have interacted with the testing region(s). In the example of FIGS. 1A to 1C there are five testing regions, and so at step S216 the application determines whether respective indicators for which each of the respective testing regions are sensitive have interacted with the testing regions. As described, the testing regions can be colour change pads. A colour change pad changes colour when an indicator to which it is sensitive is present in applied urine.

The application determines whether the indicator to which the first testing region 109-1 is sensitive has interacted with the first testing region 109-1 by determining whether the closest reference colour is a reference colour that is indicative of the analyte having interacted with the testing region. The test can be considered positive when the closest reference colour is a reference colour that is predetermined to be a positive indication colour, or belongs to a positive indication colour range, that is indicative of the analyte having interacted with the testing region. The test can be considered negative when the closest reference colour is not a reference colour that is predetermined to be a positive indication colour, or belongs to a positive indication colour range. In some examples, the determination can also include determining a numerical value of the analyte e.g. pH and SG. In some further examples, a combination of results are utilised, for example, combinations of positive/negative results and numeric results. For some types of colour change pad, reference colours can correspond to a specific value; the closest reference colour to the detected colour can then be indicative of the analyte level of the applied sample, and this determined value can be used in the determination of a condition in the bodily system of the person who provided the sample. The application repeats the process of determining whether analytes have interacted with testing regions for each of the testing regions. Determining whether the person who supplied the sample has the bodily condition for which the test is arranged to detect can involve compiling the results of each of the testing regions. For example, each testing region may be configured to test for a different indicator, and more than one indicator (or indeed all of the indicators) may need to be determined as present to reach the determination that the person who supplied the sample has the bodily condition for which is being tested.

When the determination at step S216 is complete, the process progresses to step S218.

In an alternative, step S216 may occur before step S214. In this way, it can be determined whether the indicator has interacted with the testing region before the colour of the next testing region is detected.

At step S218, the application outputs a result. The result can be displayed on a display of the electronic device. Alternatively or additionally, the result can be output in an audible manner by a speaker of the electronic device. The result indicates whether the urine applied to the card contains the indicators of the condition for which the card is configured to detect; that is, the output indicates whether or not the person whose urine has been applied to the card has the condition in their bodily system that the card is configured to test for.

The description now returns to step S212, and the determination of an error in the image data for a testing region.

When an error is determined at step S212, the process progresses step S224. In an alternative, when an error is determined at step S212, the process progresses step S222 as will be described subsequently.

At step S224 the application terminates the bodily fluid testing process and configures the electronic device to indicate that the bodily fluid testing process cannot be carried out, for example by outputting a notification that the test has failed. In an example, outputting the notification may comprise indicating on a display screen of the electronic device that the test has failed due to an error. The bodily fluid testing process may be terminated before processing the remaining testing regions following the determination of an error at step S212.

In some cases, rather than progressing directly from step S212 to step S224 in the case of the determination of an error, it may be possible capture a replacement image in order reattempt the bodily fluid test. The colour change pads may only have a limited lifetime when exposed to the urine; for colour change pads with a longer lifetime, sufficient time may be available to capture a replacement image, however for colour change pads with a shorter lifetime this may not be possible. The application can determine whether the card 100 is suitable to be processed with a replacement image based upon parameters indicated in the QR code 111. Steps S222 and S226 provide an optional process by which the replacement image can be captured.

If for example, the error determined at step S212 is due to background lighting or shadowing, or a user's finger or thumb obscuring the testing region, capturing a replacement image is advantageous as it allows for the test to be repeated with the error addressed. This improves the likelihood of the bodily fluid test being successful.

In examples, a replacement image can only be capture once. As noted above, colour change pads may only have a limited lifetime, and so repeated capturing of replacement images may coincide with degradation of the colour change pads which can result in the test no longer being useful. At step S222 it is determined whether a replacement image has already been captured. A replacement image may have already been captured when, for the testing region or one of the preceding testing regions, it has already been determined that the difference score between the detected colour and the closest reference colour is not below the respective maximum difference score, or optionally the closest reference colour does not belong to a set of one or more predetermined reference colours associated with the respective testing region. If such a replacement image has already been captured due to an error in the detected colour of a testing region, the application determines this, and progresses to step S224, outputting the test failure, rather than capturing a further replacement image. For example, if a replacement image is captured due to the determination of an error in the detected first colour of the first testing region 109-1, the application will not then capture a replacement image if another error is subsequently determined for the detected second colour of the second testing region 109-2. Likewise, if a replacement image is captured due to the determination of an error in the detected first colour of the first testing region 109-1, the application will not then capture a replacement image if an error is again determined in the updated detected first colour of the first testing region 109-1 in the replacement image.

Whilst in the preceding description, it is described that only replacement image can be captured, in alternative embodiments more than one replacement image can be captured if the testing regions (or colour change pads) have a suitable lifetime to accommodate this without affecting the integrity of the bodily fluid test process.

If the application determines that a replacement image (or replacement image data) has not already been captured, the process continues to step S226.

At step S226 the application prompts the user to capture a replacement image of the card using the camera of the electronic device upon which the application is loaded, and configures the electronic device to capture the replacement image, in a similar manner to that at step S202.

In some examples, before capturing the replacement image data, the user may be prompted to ensure that the conditions for the replacement image are favourable. For example the user may be prompted to check that the card is exposed to suitable lighting, not in a shadow, or to check that a finger or thumb is not obscuring a testing region.

The replacement image data is processed in place of the image data for which an error was determined at step S212 (hereinafter referred to as the original image data).

To ensure that the replacement image is captured before the testing regions degrade, the application can start a timer for capturing the replacement image when prompting the user to capture the replacement image; this timer can be displayed to the user. The timer sets a time limit for capturing the replacement image. When a replacement image is not captured within the time limit, the application can terminate the bodily fluid testing process and output a test failure notification, as at step S224. When a replacement image is captured within the time limit, the process continues from step S226 to step S204. In some examples, the time limit is preset within the application, for example for 2 minutes. In other examples, the time limit is dependent on the type of test being carried out and can be determined from parameters determined from the QR code 111.

Ensuring that replacement image data is captured within the time limit improves reliability in the bodily fluid test as it obviates the test being carried out on potentially degraded testing regions.

The processing steps of S204 to S212 are carried out for the first testing region 109-1 in the replacement image data. These steps correspond to those described with reference to steps S204 to S212 carried out for the first testing region 109-1 in the original image data, but are instead carried out on the replacement image data, and are summarised below. It will be understood that the processing steps described with reference to steps S204 to S212 carried out for the first testing region 109-1 in the original image data are applicable to steps S204 to S212 carried out for the first testing region 109-1 in the replacement image data.

When step S204 is repeated for the replacement image data, the application detects an updated colour of the first testing region 109-1 in the replacement image data.

When step S206 is repeated for the replacement image data, the application compares the detected updated first colour to the one or more reference colours.

When step S208 is repeated for the replacement image data, the application determines respective difference scores between the detected updated first colour and each of the one or more reference colours.

When step S210 is repeated for the replacement image data, the application determines an updated closest reference colour of the one or more reference colours to the detected updated first colour. The updated closest reference colour to the detected updated first colour has a lowest difference score compared to the detected updated first colour.

When step S212 is repeated for the replacement image data, the application determines whether the difference between the detected updated first colour and the updated closest reference colour is less than the predetermined maximum difference score. When the difference score is less than the maximum difference score, for the first testing region 109-1 in the replacement image data, the process continues to step S214. When the difference score is not less than the maximum difference score, for the first testing region 109-1 in the replacement image data, the process continues to step S224 (or optionally S222 in the case that more than one replacement image can be captured).

Upon reaching step S214, after processing the first testing region 109-1 in the replacement image data, in the example of FIGS. 1A to 1C, the process continues to step S220 and repeats steps S204 to S212 for the second testing region 109-2, the third testing region 109-3, the fourth testing region 109-4 and the fifth testing region 109-5 in the replacement image data. More generally, the steps S204 to S212 can be repeated for any number of testing regions 109 that are present in the replacement image data of the card 100.

When it is determined, at S214, that all of the testing regions in the replacement image data have been processed, the process flow continues to steps S216. Steps S216 and S218 are carried out in the same way for the replacement image data as described for the original image data.

Whilst the preceding description describes processing the detected updated first colour of the first testing region 109-1, it will be understood that the same process can occur for processing a detected updated second colour of a second testing region 109-2, and updated further colours of any further testing regions.

In some examples, all of the testing regions are processed in the replacement image data. This can improve consistency in the processing of each testing region.

In other examples, the processing in steps S204 to S212 may be carried out for each testing region using the original image data. If errors are determined for any of these testing regions, they are flagged. The replacement image data process can then be carried out only for these flagged regions. In this example, when these errors are only determined in the original image data for some but not all of the testing regions, replacement image data can be captured and then processed only for the flagged testing regions that have been determined to be erroneous in the original image data. This can reduce the processing burden as testing regions that have already been processed need not be re-processed.

In an alternative to the process flow described with reference to FIG. 2, the image can be captured on the electronic device (such as a smartphone), when prompted through the application, and then transmitted from the electronic device to a server by the application. The processing steps described with reference S204 to S224 can then be carried out by the server. In this example, the outputting of result (step S218) can comprise the server sending result to electronic device and instructing the electronic device to display the result on a display screen. The outputting of the test failure notification (S224) can comprise the server sending an instruction to report a test failure to the electronic device, thereby instructing the electronic device to display the test failure notification on a display screen.

When the server determines that replacement image data is to be captured, the server can send an instruction to capture the replacement image data to the electronic device following step S222. The electronic device can then prompt the user to capture the replacement image data (step S226), and the electronic device can then transmit this replacement image data to the server for processing the processing steps described with reference to S204 to S224 for the replacement image data.

Figure 3:
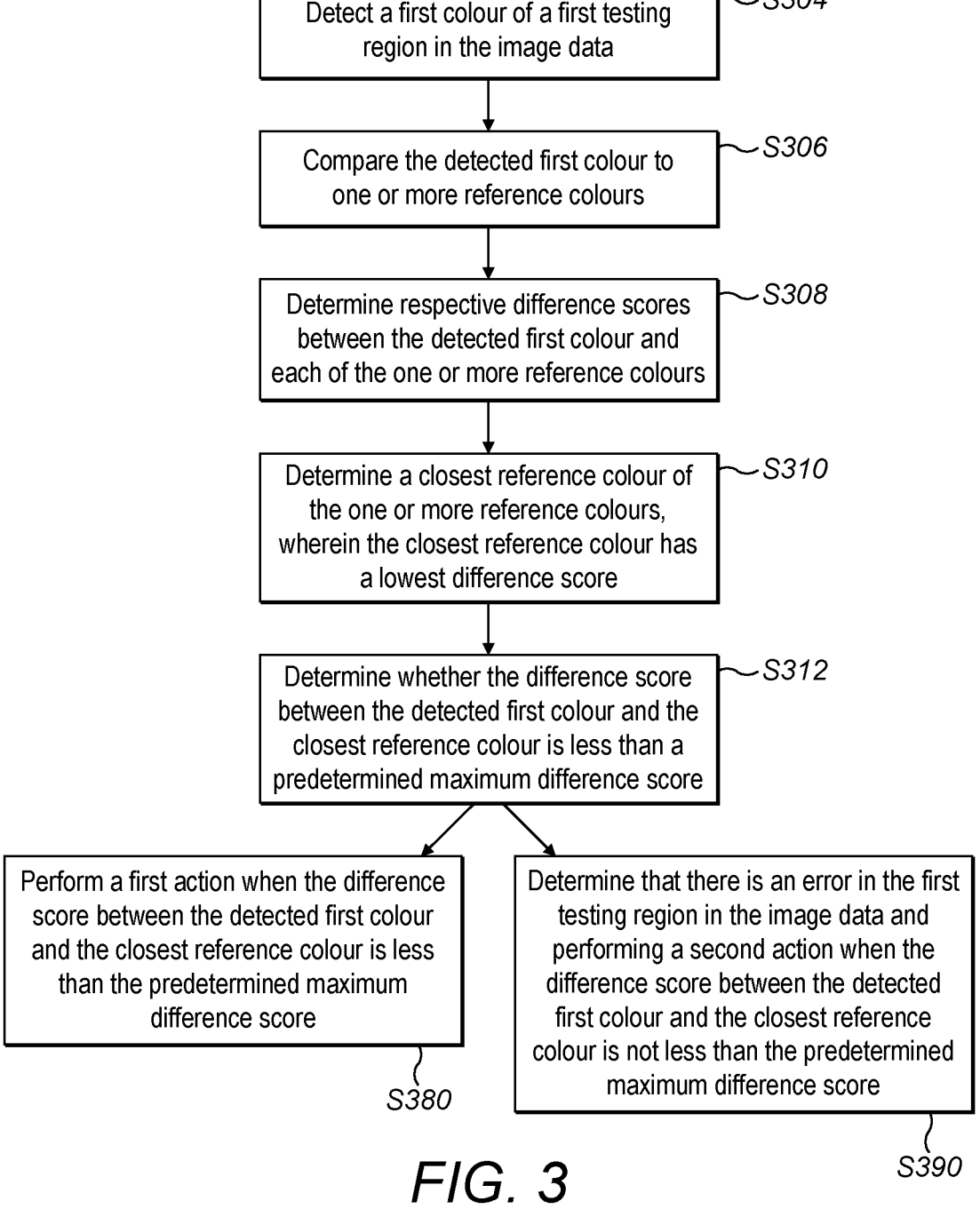
FIG. 3 is a flow diagram of processing steps involved in determining an error in image data of bodily fluid testing equipment.

FIG. 3 presents a specific process flow relating to the error determination process for the first testing region 109-1, described with reference to FIG. 2. The steps of Figure may be carried out by the application at the electronic device; alternatively, the steps may be carried out at the server following transmission of the image data from the electronic device to the server by the application.

At step S304 the first colour of the first testing region in the image data is detected (as described with reference to S204 in FIG. 2).

At step S306, the detected first colour is compared to one or more reference colours (as described with reference to step S206 in FIG. 2).

At step S308, respective difference scores between the detected first colour and each of the one or more reference colours are determined (as described with reference to step S208 in FIG. 2).

At step S310, a closest reference colour of the one or more reference colours is determined, wherein the closest reference colour has a lowest difference score (as described with reference to step S210 in FIG. 2).

At step S312, it is determined whether the difference score between the detected first colour and the closest reference colour is less than a predetermined maximum difference score (as described with reference to step S212 in FIG. 2).

At step S380 a first action is performed when the difference score between the detected first colour and the closest reference colour is less than the predetermined maximum difference score. This can be considered determining that there is not an error based upon the difference score between the detected first colour and the closest reference colour.

Performing the first action can comprise determining whether an indicator has interacted with the first testing region 109-1 based upon the detected first colour (as described with reference to step S216 in FIG. 2).

When the bodily fluid testing region comprises a plurality of further testing regions (for example the second testing region 109-2, third testing region 109-3, fourth testing region 109-4 and fifth testing region 109-4 in the example of FIGS. 1A to 1C, or more generally a second testing region 109-2 to an nth testing region) having further colours in the image data, performing the first action can comprise repeating the steps S204 to S212 for each respective further testing region (as described with reference to step S220 of FIG. 2). More generally, when a bodily fluid testing card as n testing regions, the first action can comprise repeating steps S204 to S212 for the second testing region 109-2 to the nth testing region. That is, the first action can further comprise determining whether an indicator has interacted with the first testing region 109-1 based upon the detected first colour and whether respective indicators have interacted with the further testing regions based upon the detected respective further colours when the difference scores between each respective detected further colour and the respective closest reference colour is less than a respective predetermined maximum difference score.

The first action can further comprise outputting a result corresponding to whether an indicator has interacted with the first testing region 109-1 (as described with reference to step S218 of FIG. 2), and if there are further testing regions whether respective indicators have interacted with the further testing regions.

At step S390 it is determined that there is an error in the first testing region 109-1 in the image data, and a second action is performed, when the difference score between the detected first colour and the closest reference colour is not less than the predetermined maximum difference score.

Performing the second action can comprise configuring the electronic device to indicate that the bodily fluid testing process cannot be carried out, and can also comprise terminating the bodily fluid testing process (as described with reference to step S224 of FIG. 2).

Alternatively, the second action can comprise configuring the electronic device to capture replacement image data (as described with reference to steps S222 and S226 of FIG. 2). In some examples, the electronic device is configured to capture the replacement image data only within a predetermined time limit.

Figure 4:
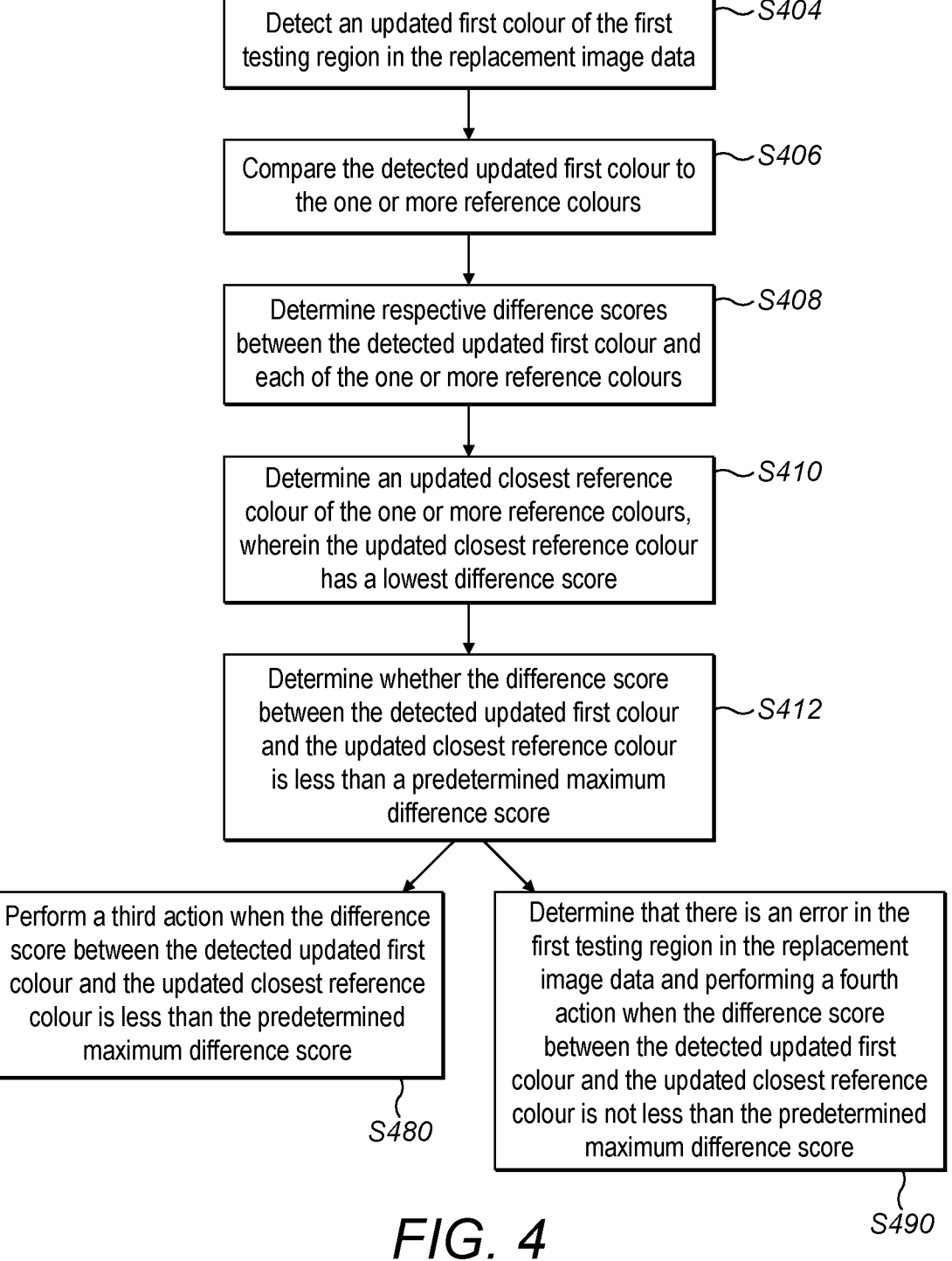
FIG. 4 is a flow diagram of processing steps involved in determining an error in replacement image data of bodily fluid testing equipment.

FIG. 4 presents a specific process flow relating to the error determination process for replacement image data, which for example can take place following the determination at step S212 of FIG. 2 (or S312 of FIG. 3) that there is an error, and the capturing of the replacement image data.

At step S404, an updated first colour of the first testing region 109-1 in the replacement image data is detected (as described with reference to step S204 in FIG. 2 for the replacement image data).

At step S406, the detected updated first colour is compared to the one or more reference colours (as described with reference to step S206 in FIG. 2 for the replacement image data).

At step S408, respective difference scores between the detected updated first colour and each of the one or more reference colours are determined (as described with reference to step S208 in FIG. 2 for the replacement image data).

At step S410, an updated closest reference colour of the one or more reference colours is determined, wherein the updated closest reference colour has a lowest difference score (as described with reference to step S210 in FIG. 2 for the replacement image data).

At step S412, it is determined whether the difference score between the detected updated first colour and the updated closest reference colour is less than the predetermined maximum difference score (as described with reference to step S212 in FIG. 2 for the replacement image data).

At step S480 a third action is performed, when the difference score between the detected updated first colour and the updated closest reference colour is less than the predetermined maximum difference score. This can be considered determining that there is not an error based upon the difference score between the updated detected first colour and the closest reference colour.

Performing the third action can comprise determining whether an indicator has interacted with the first testing region 109-1 based upon the detected updated first colour (as described with reference to step S216 in FIG. 2 for the replacement image data).

When the bodily fluid testing region comprises a plurality of further testing regions (for example the second testing region 109-2, third testing region 109-3, fourth testing region 109-4 and fifth testing region 109-4 in the example of FIGS. 1A to 1C, or more generally a second testing region 109-2 to an nth testing region) having further updated colours in the replacement image data, performing the third action can comprise repeating the steps S204 to S212 for each respective further testing region (as described with reference to step S220 of FIG. 2 for the replacement image data) in the replacement image data. The third action can further comprise determining whether an indicator has interacted with the first testing region 109-1 based upon the detected updated first colour and whether respective indicators have interacted with the further testing regions based upon the respective detected updated further colours when the difference scores between each respective detected updated further colour and the respective updated closest reference colour is less than a predetermined maximum difference score.

At step S490, it is determined that there is an error in the first testing region 109-1 in the replacement image data, and a fourth action is performed, when the difference score between the detected updated first colour and the updated closest reference colour is not less than the predetermined maximum difference score.

Performing the fourth action can comprise configuring the electronic device to indicate that the bodily fluid testing process cannot be carried out, and can also comprise terminating the bodily fluid testing process (as described with reference to step S224 in FIG. 2 for the replacement image data).

Figure 5:
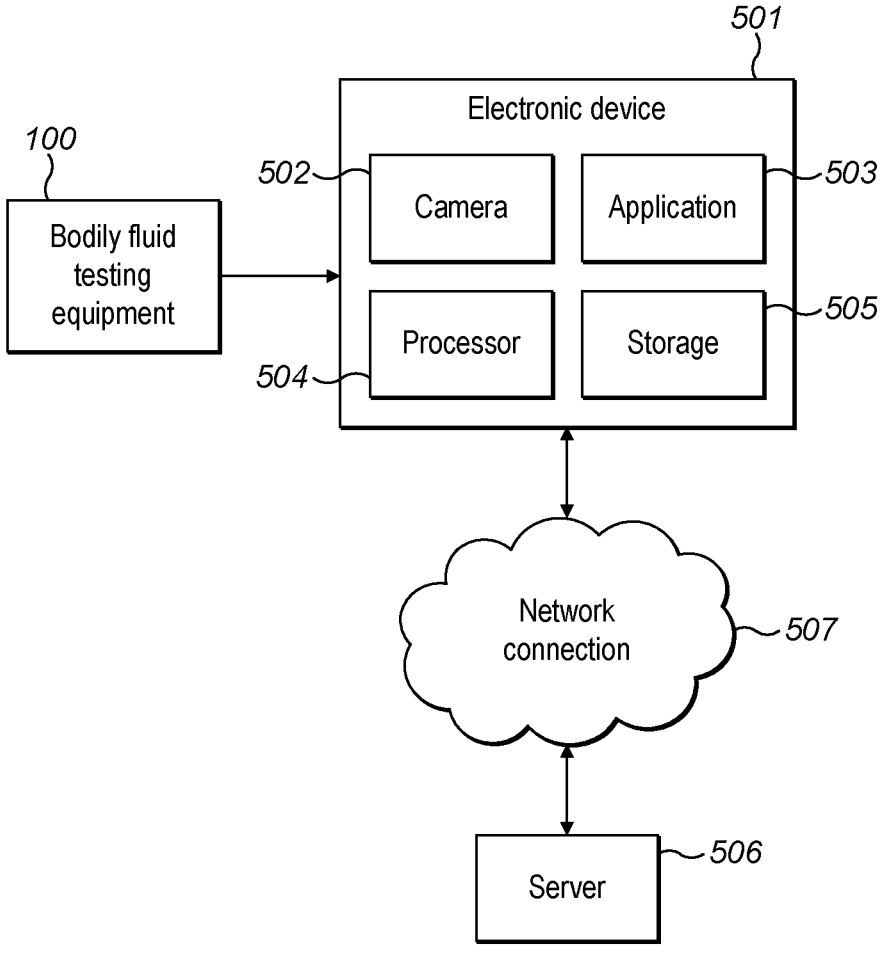
FIG. 5 is a block diagram of hardware entities in bodily fluid testing systems according to embodiments of the disclosure.

FIG. 5 presents a block diagram of the hardware entities in the bodily fluid testing system of the present disclosure. The electronic device 501, such as a smartphone, comprises a camera 502. The electronic device 501 has an application 503 stored thereon arranged to perform the methods previously described in the present description. The electronic device 501 further has a processor 504 (or a plurality of processors) arranged to execute the application. The electronic device 501 further includes storage 505; the storage 505 storing code executable by the processor 504 to execute the application 503 as well as parameters relating to the application 503. The code can comprise instructions that cause the processor to execute the processing steps described with reference to FIGS. 2 to 4. The camera 502 is arranged to capture image data, or photograph(s), of the bodily fluid testing equipment or card 100 as previously described in the present description. In some examples the application 503 carries out the previously described processes locally. In other examples, the previously described processes are at least partially carried out at a server 506. In such a case, the electronic device 501 is connected to the server 506 by a network connection 507, for example an internet connection or a 4G or 5G data connection (amongst any other suitable network connection means). The electronic device 501 and the server 506 exchange communications using the network connection 507.

It will be readily understood to the skilled person that the preceding embodiments are not limiting in that features of each embodiment may be incorporated into the other embodiments as appropriate.

The processing steps described herein carried out by the electronic device may be stored in a non-transitory computer-readable medium, or storage, associated with the electronic device. A computer-readable medium can include non-volatile media and volatile media. Volatile media can include semiconductor memories and dynamic memories, amongst others. Non-volatile media can include optical disks and magnetic disks, amongst others.

The invention claimed is:

1. A method for determining an error in image data of bodily fluid testing equipment in a bodily fluid testing process, the image data captured by an electronic device, and the method comprising:
   detecting a first colour of a first testing region in the image data;
   comparing the detected first colour to a series of reference colours;
   determining respective difference scores between the detected first colour and each reference colour of the series of reference colours;
   determining a closest reference colour of the series of reference colours, wherein the closest reference colour has a lowest difference score;
   determining whether the difference score between the detected first colour and the closest reference colour of the series of reference colours is less than a predetermined maximum difference score;
   performing a first action when the difference score between the detected first colour and the closest reference colour of the series of reference colours is less than the predetermined maximum difference score; and
   determining that there is an error in the first testing region in the image data and performing a second action when the difference score between the detected first colour and the closest reference colour of the series of reference colours is not less than the predetermined maximum difference score; wherein the second action comprises:
      configuring the electronic device to capture replacement image data, wherein the electronic device is configured to capture the replacement image data only within a predetermined time limit, and the time limit is predetermined to end before the first testing region degrades.

2. The method of claim 1, wherein the first testing region is a first colour change pad configured to change colour in presence of one or more specific indicators.

3. The method of claim 1, further comprising:
   determining whether the closest reference colour of the series of reference colours belongs to a set of one or more predetermined reference colours associated with the first testing region; and
   determining that there is an error in the first testing region in the image data and performing the second action when the closest reference colour of the series of reference colours does not belong to the set of one or more predetermined reference colours.

4. The method of claim 1, wherein the first action comprises:
   determining whether an indicator has interacted with the first testing region based upon the detected first colour.

5. The method of claim 1, wherein the bodily fluid testing equipment comprises a plurality of further testing regions having respective further colours in the image data, and the first action comprises repeating the steps of claim 1 for each respective further testing region; and
   determining whether an indicator has interacted with the first testing region based upon the detected first colour and whether respective indicators have interacted with the further testing regions based upon the detected respective further colours when the difference scores between each respective detected further colour and the respective closest reference colour of the series of reference colours is less than a predetermined maximum difference score.

6. The method of claim 1, wherein the second action comprises:

configuring the electronic device to indicate that the bodily fluid testing process cannot be carried out.

7. The method of claim 1, further comprising:

detecting an updated first colour of the first testing region in the replacement image data;

comparing the detected updated first colour to the series of reference colours;

determining respective difference scores between the detected updated first colour and each reference colour of the series of reference colours;

determining an updated closest reference colour of the series of reference colours, wherein the updated closest reference colour of the series of reference colours has a lowest difference score;

determining whether the difference score between the detected updated first colour and the updated closest reference colour of the series of reference colours is less than the predetermined maximum difference score;

performing a third action when the difference score between the detected updated first colour and the updated closest reference colour of the series of reference colours is less than the predetermined maximum difference score; and determining that there is an error in the first testing region in the replacement image data and performing a fourth action when the difference score between the detected updated first colour and the updated closest reference colour of the series of reference colours is not less than the predetermined maximum difference score.

8. The method of claim 7, wherein the third action comprises determining whether an indicator has interacted with the first testing region based upon the detected updated first colour; and/or wherein the fourth action comprises configuring the electronic device to indicate that the bodily fluid testing process cannot be carried out.

9. The method of claim 1, wherein the respective difference scores between the detected first colour and each reference colour of the series of reference colours are determined as Delta E values between the detected first colour and each reference colour of the series of reference colours.

10. The method of claim 1, wherein the method is performed at the electronic device; or wherein the image data is transmitted from the electronic device to a server and the method is performed at the server.

11. An electronic device configured to perform the method of claim 1.

12. A server configured to perform the method of claim 1.

13. A non-transitory computer-readable medium storing instructions which when executed by one or more processors cause the processors to perform the method of claim 1.

\* \* \* \* \*